(12) United States Patent
Wang et al.

(10) Patent No.: US 11,953,500 B2
(45) Date of Patent: Apr. 9, 2024

(54) DETECTION REAGENT AND THERAPEUTIC TARGET FOR B CELL TUMOR AFTER TARGETED THERAPY AND RELATED APPLICATION

(71) Applicants: Synarc Research Laboratory (Beijing) Ltd., Beijing (CN); HEBEI YANDA LUDAOPEI HOSPITAL, Langfang (CN)

(72) Inventors: Hui Wang, Beijing (CN); Man Chen, Beijing (CN); Aixian Wang, Beijing (CN); Meiwei Gong, Beijing (CN); Xueying Wu, Beijing (CN); Junyi Zhen, Beijing (CN); Qing Du, Beijing (CN); Ya Guo, Beijing (CN)

(73) Assignees: Synarc Research Laboratory (Beijing) Ltd., Beijing (CN); HEBEI YANDA LUDAOPEI HOSPITAL, Sanhe (CN)

( * ) Notice: Subject to any disclaimer, the term of this patent is extended or adjusted under 35 U.S.C. 154(b) by 57 days.

(21) Appl. No.: 17/824,162

(22) Filed: May 25, 2022

(65) Prior Publication Data

US 2023/0074660 A1  Mar. 9, 2023

(30) Foreign Application Priority Data

Sep. 2, 2021  (CN) .......................... 202111023887.2

(51) Int. Cl.
*G01N 33/543* (2006.01)
*G01N 15/14* (2006.01)
*G01N 33/569* (2006.01)
*G01N 33/574* (2006.01)
*G01N 33/577* (2006.01)
*G01N 33/58* (2006.01)

(52) U.S. Cl.
CPC ....... *G01N 33/56966* (2013.01); *G01N 15/14* (2013.01); *G01N 33/57426* (2013.01); *G01N 33/57492* (2013.01); *G01N 33/577* (2013.01); *G01N 33/582* (2013.01); *G01N 2333/70503* (2013.01); *G01N 2333/70589* (2013.01); *G01N 2333/70596* (2013.01); *G01N 2469/10* (2013.01)

(58) Field of Classification Search
None
See application file for complete search history.

(56) References Cited

U.S. PATENT DOCUMENTS 4,444,879 A * 4/1984 Foster ................ G01N 33/6854
435/805
6,475,364 B1 * 11/2002 Dubrow ........... G01N 27/44791
422/68.1

FOREIGN PATENT DOCUMENTS

| CN | 109655616 A | 4/2019 |
|----|-------------|--------|
| CN | 109912683 A | 6/2019 |
| CN | 112552407 A | 3/2021 |
| JP | 2004-163121 A | 6/2004 |
| WO | WO-2021/041299 A1 | 3/2021 |

OTHER PUBLICATIONS

Fuda et al., Minimal/Measurable Residual Disease Detection in Acute Leukemias by Multiparameter Flow Cytometry, Current Hemtologic Malignancy Reports, Nov. 2019, pp. 1-12. (Year: 2018).*
Jamin et al., Modulation of CD72 by ligation of B cell receptor complex molecules on CD5+ B cells, International Immunology, vol. 9 , No. 7, pp. 1001-1009. (Year: 1997).*
Collective Publication: Panel Proposal for the Immunophenotypic Diagnosis of Hematological Malignancies, a collaborative Consensus from the Groupe d'Etude Immunologique des Leuce-mies (GEIL), Cytometry Part B 2018; 94B, pp. 542-547. (Year: 2018).*
Roy et al., Flow Cytometry APC-Tandem Dyes Are Degraded Through a Cell-Dependent Mechanism, Cytometry Part A, 75A, 2009, pp. 882-890. (Year: 2009).*
ODonahue et al., Antibody Cocktail Validation for Flow Cytometry, International Clinical Cytometry Society, Nov. 26, 2019, pp. 1-11. (Year: 2019).*
First Office Action and Search Report for Chinese Application No. 202111023887.2, dated Oct. 13, 2021, 17 pages, English portions only.
Garand et al., CD72 is Constantly Expresed in Chronic Lymphocytic-Leukemi A and Other B-Cell Lymphoproliferative Disorders, Leukemia Research, vol. 18, No. 8, 1994, 2 pages.
Notification to Grant and Supplementary Search Report Chinese Application No. 202111023887.2, dated Oct. 30. 2021, 4 pages, English portions only.
Yan-Rong et al., Clinical significance for minimal residual disease detection by 4 color flow cytometry in adult and childhood B lineage acute lymphoblastic leukemia, Chin J Hematol, May 2006, vol. 27 No. 5, 6 pages.

* cited by examiner

*Primary Examiner* — Gary Counts
(74) *Attorney, Agent, or Firm* — FOLEY & LARDNER LLP

(57) ABSTRACT

The present invention provides a detection reagent and therapeutic target for B cell tumor after targeted therapy and related applications. The reagent composition comprises 3 groups of antibodies, with the first group of antibodies including an anti-CD38 antibody, an anti-CD10 antibody, an anti-CD34 antibody, an anti-CD19 antibody, an anti-CD24 an antibody, an anti-CD20 antibody, an anti-CD81 antibody, an anti-CD45 antibody; the second group of antibodies including an anti-CD38 antibody, an anti-CD10 antibody, an anti-CD34 antibody, an anti-CD19 antibody, an anti-CD20 antibody, an anti-CD72 antibody, an anti-CD45 antibody; and the third group of antibodies including an anti-cytoplasmic CD79a antibody. The reagent composition of the present invention can be applied for the detection of B-lymphocyte tumors after targeted therapy by flow cytometry.

6 Claims, 10 Drawing Sheets

DETECTION REAGENT AND THERAPEUTIC TARGET FOR B CELL TUMOR AFTER TARGETED THERAPY AND RELATED APPLICATION

CROSS-REFERENCE TO RELATED APPLICATION

This application claims priority to Chinese Patent Application No. 202111023887.2, filed on Sep. 2, 2021, which is hereby incorporated by reference in its entirety.

TECHNICAL FIELD

The present invention relates to a detection reagent and therapeutic target for B-cell tumors after targeted therapy and related applications, specifically, to a reagent composition, kit, detection device, therapeutic target for flow cytometric detection of B-cell tumor after targeted therapy, and related applications, which belongs to the field of hematopathological detection and therapy technology.

BACKGROUND

Acute lymphoblastic leukaemia (ALL)/lymphoblastic lymphoma (LBL) is a common acute leukaemia, of which 80-85% is B-ALL/LBL. Among childhood leukemias in particular, acute lymphoblastic leukemia is the most prevalent, accounting for almost 80% of childhood acute leukemias and more than 30% of acute leukemias in adults. During the days without targeted therapy, these poor prognostic B-ALL/LBL such as persistent positive minimal residual disease (MRD) and/or poor prognostic genetics have a long-term survival rate of only 20-30%, even after allogeneic hematopoietic stem cell transplantation (allo-HSCT). In recent years, progress has been made in targeted therapies, particularly CD19-Chimeric Antigen Receptors T cells (CAR-T) for B-ALL and CD3/CD19 bispecific antibody therapy for B-ALL, both of which have achieved a complete remission (CR) rate of 90% or more in the treatment of refractory/relapsed (r/r) B-ALL. However, current CAR-T and bispecific immunotherapies and other related targeted therapies for B-ALL have high relapse rates when used alone, many hospitals employ bridging hematopoietic stem cell transplantation (HSCT) shortly after immunotherapy, for example within 2 months. Numerous studies have shown that no matter what kind of method used to achieve CR before allo-HSCT, the same success rate and survival rate can be achieved as bridging allo-HSCT after achieving CR with conventional chemotherapy, which means that before the target therapy era, these r/r B-ALL/LBL patients who could not achieve CR with conventional therapies and received allo-HSCT with minimal residual diseases (MRD) only had a five-year survival rate of 20%-30% after allo-HSCT, while 90% or more of the patients could achieve remission with a targeted therapy, and with bridging transplantation, the five-year survival rate would increase to 70%-80%, which may save the lives of many B-ALL/LBL patients. Another type of disease that has been successfully treated by CAR-T is mature B-cell neoplasms, the vast majority of which express CD19, making CD19-CAR-T therapy a major breakthrough for B-cell lymphoma as well.

MRD detection is critical because targeted therapies can be repeated use, or in case of failure CD19-CAR-T can be followed by CD22-CAR-T, or dual targeting CAR-T, or both CAR-Ts can be performed in combination. Studies have shown the importance of MRD detection and the evaluation of CD19 or other promising targets' expression on MRD positive cells at different time point after targeted therapy, for example, before bridging transplantation, and after bridging transplantation. Flow Cytometry (FCM) is currently the most common, popular and cost-effective clinical assay for MRD detection. In particular, target selection prior to treatment with CAR-T and targeted therapies, as well as post-treatment efficacy assessment and determination of the next step in the regimen, are of great clinical importance for the application of appropriate targeted therapies.

However, there are three critical issues after CD19-CAR-T: (1) 13-68% of cases are CD19 dim or negative (neg) expression at the time of relapse, and the MRD detection by FCM is more difficult because 100% of clinical FCM laboratories use CD19/SSC to set up B-cell gates for MRD detection, which means that 13%-68% of cases are at risk of missed diagnosis. (2) Conventional MRD detection protocols set rough B gate with only one B lineage marker CD19, and do not involve in screening for other targets after CD19-negative relapse, which lacks guidance for CD19neg relapse cases. (3) In addition, the current MRD detection by FCM is difficult and has a high level of human participation, which is disadvantageous for the development of flow cytometry, and artificial intelligence is the trend for the future development of MRD detection technology.

In the prior art, explorative investigations have been done by researchers, including an investigation done by the University of Washington for MRD detection after a CAR-T cell infusion therapy by B cell gating with CD22positive (pos) in combination with CD24pos/CD66c neg, which has a limited significance. CN112552407A discloses a method for detecting MRD, by combinational gating with multiple markers using CD19 and cytoplasmic (c) CD79a dual B lineage markers, which is effective at a certain level for selecting CD19neg and CD19 pos B cells by gating, covering the most complete immature B cell populations, or even B cell populations, and reducing the probability of missed diagnosis.

SUMMARY OF THE INVENTION

An object of the present invention is to provide a reagent composition for flow cytometric detection of B-cell tumors after targeted therapy for more efficient flow cytometric detection of B-cell tumors after targeted therapy.

Another object of the present invention is to provide related application of the reagent composition for flow cytometric detection of B-cell tumors after targeted therapy.

A further object of the present invention is to provide a device for flow cytometric detection of B-cell tumors after targeted therapy.

Yet another object of the present invention is to provide a new promising therapeutic target for B-cell tumors and its related application.

In one aspect, the present invention provides a reagent composition comprising a first group of antibodies, a second group of antibodies, and a third group of antibodies, wherein:

the first group of antibodies includes: an anti-CD38 antibody, an anti-CD10 antibody, an anti-CD34 antibody, an anti-CD19 antibody, an anti-CD24 antibody, an anti-CD20 antibody, an anti-CD81 antibody, an anti-CD45 antibody;

the second group of antibodies includes: an anti-CD38 antibody, an anti-CD10 antibody, an anti-CD34 antibody, an anti-CD19 antibody, an anti-CD20 antibody, an anti-CD72 antibody, an anti-CD45 antibody;

the third group of antibodies includes: an anti-cytoplasmic CD79a antibody;

the reagent composition is a composition useful for flow cytometric detection of B cell tumors after targeted therapy, and is used by applying a two-tube parallel protocol, wherein the second group of antibodies and the third group of antibodies are used for the sample in the same tube.

The reagent composition of the present invention can be used for flow cytometric detection of MRD of B-cell tumors after targeted therapy, mainly for B-lineage acute lymphoblastic leukemia (ALL)/lymphoblast lymphoma (LBL), especially in cases where B-cell markers such as CD19 and/or CD22 or even BAFFR and more are dim or negative after targeted therapy, and gating is effectively set for the selection of B-cells, including CD19neg and CD19pos B-cells. In some specific embodiments of the present invention, the B-cell tumor is B-cell acute lymphoblastic leukemia or B-cell non-Hodgkin's lymphomas, and the B-cell non-Hodgkin's lymphomas include Burkitt's lymphoma, chronic lymphocytic leukemia, diffuse large B-cell lymphoma, follicular lymphoma, hairy cell leukemia, lymphoplasmacytic lymphoma, mantle cell lymphoma, marginal zone lymphoma, or small cell lymphoma. In a specific application, a two-tube parallel protocol is used, both tubes are subjected to B cell gate detection by using double markers, CD19 and CD24 or triple markers, CD19, cCD79a and CD72, in combination, while assaying the loss and expression of a certain pan-B marker, and a B-cell phenotype analysis is conducted by using five parameters of CD10, CD34, CD20, CD38, and CD45, or six parameters of CD10, CD34, CD20, CD38, CD45 in combination with CD81. By using the reagent composition of the present invention for flow cytometric detection, it can be achieved that the most entire immature B-cell populations, or even B-cell populations are maximally covered and the probability of missed diagnosis is minimized, especially for follow-up cases after targeted treatment for B-cell markers such as CD19, CD22, BAFFR, or primary cases where these markers are negatively or weakly expressed.

According to a specific embodiment of the present invention, each antibody in the reagent composition of the present invention is a monoclonal antibody.

According to a specific embodiment of the present invention, each antibody in the reagent composition of the present invention is a fluorescent-labeled antibody. Preferably, in the first group of antibodies, the fluorescent labels for the anti-CD38 antibody, anti-CD10 antibody, anti-CD34 antibody, anti-CD19 antibody, anti-CD24 antibody, anti-CD20 antibody, anti-CD81 antibody, and anti-CD45 antibody are in this order FITC, PE, PerCP-Cy5.5, PE-Cy7, APC, APC-Cy7, BV421, and V500, respectively. In the second group of antibodies, the fluorescent labels for the anti-CD38 antibody, anti-CD10 antibody, anti-CD34 antibody, anti-CD19 antibody, anti-CD20 antibody, anti-CD72 antibody, and anti-CD45 antibody are, in this order, FITC, PE, PerCP-Cy5.5, PE-Cy7, APC-Cy7, BV421, and V500, respectively. In the third group of antibodies, the fluorescent label for the anti-cytoplasmic CD79a antibody is APC. By conjugating different antibodies with particular fluorophores in the present invention, it is possible to achieve excellent staining of all fluorophores in each channel when the reagent composition of the present invention is used for flow cytometric detection of B-cell tumors after targeted therapy.

According to a specific embodiment of the present invention, each antibody component of the reagent composition of the present invention is commercially available. Each antibody should meet the standard requirements in the relevant industries.

According to a specific embodiment of the present invention, the first group of antibodies in the reagent composition of the present invention is a mixture of the anti-CD38 antibody, anti-CD10 antibody, anti-CD34 antibody, anti-CD19 antibody, anti-CD24 antibody, anti-CD20 antibody, anti-CD81 antibody, and anti-CD45 antibody mixed in a volume ratio of 5:5:5:3:2:3:3:3 (in terms of substantially equivalent valence); the second group of antibodies is a mixture of anti-CD38 antibody, anti-CD10 antibody, anti-CD34 antibody, anti-CD19 antibody, anti-CD20 antibody, anti-CD72 antibody, and anti-CD45 antibody mixed in a volume ratio of 5:5:5:3:3:3:3 (in terms of substantially equivalent valence).

Another aspect of the present invention provides a kit comprising a first container, a second container and a third container, each accommodating the first group of antibodies, the second group of antibodies or the third group of antibodies of the reagent composition of the present invention, respectively.

According to a specific embodiment of the present invention, the kit of the present invention may also include one or more of selected from the group consisting of lysing solution, permeabilization reagent, buffer (Phosphate buffered solution) and flow cytometric tubes for use together with a flow cytometer. These reagents and consumables are commercially available. Here, the membrane permeabilization reagent is preferably a permeabilization reagent comprising solution A and solution B. Various reagent materials can be accommodated in separate containers.

The kit of the present invention can be used for flow cytometric detection of B-cell tumors after targeted therapy.

In another aspect, the present invention also provides use of the reagent composition in preparation of flow cytometry sample for detecting B-cell tumor after targeted therapy. In other words, the present invention provides a method for detecting B-cell tumor after targeted therapy by flow cytometry comprising preparing a flow cytometric sample after processing a sample to be tested using the reagent composition.

According to a specific embodiment of the present invention, a process for preparation of a flow cytometric sample for detecting B-cell tumor after targeted therapy comprises the steps of:

(1) adding a sample to be tested to two flow cytometric tubes A and B, respectively, with a guaranteed cell number of $1\times10^6$/tube to $1\times10^7$/tube; the sample to be tested is bone marrow or peripheral blood and in a single cell suspension state;

(2) adding the first group of antibodies in the reagent composition according to the invention to the Tube A obtained from the treatment in step (1), adding the second group of antibodies in the reagent composition according to the invention to the Tube B obtained from the treatment in step (1), and incubating each flow cytometric tube at room temperature in dark;

(3) adding the solution A of a permeabilization reagent to the flow cytometric Tube B after the incubation in step (2), and resuming the incubation at room temperature in dark;

(4) adding 1× lysing solution to the flow cytometric tube A after the incubation in step (2) and 1×lysing solution to the flow cytometric Tube B after the incubation in step (3), and resuming the incubation at room temperature in dark;

(5) centrifuging each flow cytometric tube after the incubation in step (4) and removing the supernatant;

(6) adding the solution B of the permeabilization reagent and the third group of antibodies of the reagent composition of according to the invention to the Tube B after removing the supernatant in step (5), and incubating at room temperature in dark; and (7) adding a PBS buffer to the Tube A after removing the supernatant in step (5) and to the Tube B after the incubation in step (6) respectively for washing, removing the supernatant after centrifugation, and resuspending cells with a PBS buffer to obtain the flow cytometric sample.

In the present invention, the description of the steps of operation, unless specifically stated or there is a precedence relationship that can be clearly established from the context, the order of the description is not intended to limit the actual order of these steps of operation.

According to a specific embodiment of the present invention, each reagent, except for the reagent composition of the present invention, may be used in an amount with reference to the conventional usage in the art or in accordance with the recommended dosage of the manufacturer.

According to a specific embodiment of the present invention, for the reagent composition of the present invention, the first group of antibodies is added in an amount of 15 to 58 μl/tube, the second group of antibodies is added in an amount of 14 to 54 μl/tube, and the third group of antibodies is added in an amount of 2 to 5 μl/tube.

According to a specific embodiment of the present invention, in step (1), each tube of sample is added in a volume of no more than 160 μl (for a scarce amount of peripheral blood cells from a patient, adding to a volume exceeding 160 μl, if necessary, and concentrating by centrifugation to remove the supernatant).

According to a specific embodiment of the present invention, the incubation duration in step (2) may be 10 to 30 minutes.

According to a specific embodiment of the present invention, in step (3), the incubation duration may be 5 to 20 minutes. The solution A of the permeabilization reagent may be added in an amount according to the recommended dosage of the manufacturer, usually 100 μl/tube.

According to a specific embodiment of the present invention, in step (4), the incubation duration may be 5 to 30 minutes. 1× lysing solution is added in an amount of 2 to 3 ml/tube.

According to a specific embodiment of the present invention, in step (5), the common conditions for centrifugation may be centrifugated at 1000 to 2000 rpm (or 300 to 450 g) for 5 minutes.

According to a specific embodiment of the present invention, in step (6), an incubation for about 10 to 30 minutes is necessary. The solution B of the permeabilization reagent may be added in an amount according to the recommended dosage of the manufacturer, usually 50 μl/tube.

According to a specific embodiment of the present invention, in step (7), the PBS buffer for washing is added in an amount of 2 to 3 ml/tube. The conditions for centrifugation may be centrifugated at 1000 to 2000 rpm (or 300 to 450 g) for 5 minutes. The PBS buffer for resuspension is added in an amount of 0.5 to 1 ml/tube.

Another aspect of the present invention provides a device for flow cytometric detection of B cell tumor after targeted therapy, comprising a detection unit and an analysis unit, wherein:

the detection unit comprises reagent materials for testing a sample from an individual to be tested by flow cytometry, to obtaining the test results of the sample; the reagent materials comprise the reagent composition according to the invention;

the analysis unit is configured for analyzing the test results from the detection unit.

According to a specific embodiment of the present invention, the device of the present invention for flow cytometric detection of B cell tumor after targeted therapy is used for flow cytometric detection of B-cell tumor after targeted therapy, wherein:

a process of testing a sample from an individual to be tested by flow cytometry comprises:

preparing a flow cytometric sample after processing a sample to be tested using the reagent composition of the present invention (detailed processing procedure as described above); and performing flow cytometric detection.

In other words, the method of the present invention for detecting B-cell tumor after targeted therapy by flow cytometry comprises preparing a flow cytometric sample after processing a sample to be tested using the reagent composition, further comprises performing flow cytometric detection.

Here, it is recommended to obtain at least 300,000, preferably 1,000,000 cells.

According to a specific embodiment of the present invention, during the flow cytometric analysis of B-cell tumors after targeted therapy in the present invention, combinations of any two among CD45/CD10/CD38/CD20/CD34/CD81 are used for the Tube A to analyze the expression in normal B cells at all stages within the B cell gates; combinations of any two among CD45/CD10/CD38/CD20/CD34 are used for the Tube B to analyze the expression in normal B cells at all stages within the B-cell gates. In addition, a process of multi-dimensional B-cell analysis is used, in which B-cell gates are set by using a multi-parameter multi-dimensional gating method for any positive B-cell markers (for example CD19 and/or CD24 in tube A, CD19 and/or cCD79a and/or CD72 in tube B), and the expression in B-cells with various developmental patterns is analyzed respectively with a six-parameter six-dimensional radar plot (tube A) or a five-parameter five-dimensional radar plot (tube B), where the angle of each parameter is adjusted to allow the developing B-cells at various stages to be clearly distributed in different regions, while the region having the highest probability of MRD occurrence is kept empty during the analysis of a normal control tube. The same process is employed for the analysis of samples from a patient, and any cells different from normal (DfN) are identified. According to a specific embodiment of the present invention, for the flow cytometric detection of B-cell tumor after targeted therapy according to the invention, the process of testing a sample from an individual to be tested by flow cytometric detection includes:

setting the gates for Tube A for the flow cytometric detection as follows: a single cell gate P1 is set, and a live cell gate P2 is set within the gate P1 to obtain single live cells; different groups of blood cells are gated within the gate P2 by CD45/SSC dot plot; in traditional method B cell markers CD19 and CD24 are seperately used in combination with SSC to gate CD19pos B cells and CD24pos B cells; the CD19pos and/or CD24pos B cell gate B1 is set by three-parameter three-dimensional gating of CD19, CD24 and SSC within the gate P2; six-dimensional gating is done within the gate B1 with CD45/CD10/CD38/CD20/CD34/CD81, thereby distributing the B cells in different regions according to various maturing stages; and setting the gates for Tube B for the flow cytometric detection as follows: a single cell gate P1 and a live cell gate P2 are set sequentially; different groups of blood cells are gated within the gate P2 by CD45/SSC dot plot; in traditional method CD19pos B, CD72pos B and cCD79apos B cell gates are seperately set with B cell markers CD19, CD72 and cytoplasmic CD79a in combination with SSC; the CD19pos and/or CD72pos and/or cCD79a pos B cell gate B2 is set by four-parameter four-dimensional gating of CD19, CD72, cCD79a and SSC within the gate P2; to select the promising CAR-T target for next step, a three-parameter three-dimensional gating is set with cCD79a, CD19, and CD72, while drawing a CD19neg cell gate and CD72neg cell gate (in which put cCD79a in the y axis, CD72 and CD19 on either side of x axis aiming to set CD19 pos or CD72 pos MRD), respectively; five-dimensional gating is done with CD45/CD10/CD38/CD20/CD34 within the gate B2, thereby distributing the B cells in different regions according to various maturing stages.

More specifically, during the multi-parameter multi-dimensional analysis, the 12 o'clock direction is taken as degree 0. When the angle of each coordinate axis is determined clockwise along 360 degrees, it is noteworthy that:

(1) For B-cell gating, the angels to be set are important: both the CD24 and CD19 in Tube A and the CD19, CD72, cCD79a in Tube B are expressed in normal B cells, and therefore if the two markers in Tube A are at a 180 degree angle or the three markers in Tube B are scattered at a 120 degree angle apart, the result is positioned near the center as they counteract each other due to equal or similar expression; at most a shift from the normal is observed from expression decrease due to the difference in intensity of the markers labeled with various fluorophores. For the difference in the expression of the four B cell markers involved in the present invention, under normal conditions, CD19 and cCD79a are both expressed within essentially the same range, and are found B cells as well as in normal plasma cells; CD24 and CD72 are both expressed within essentially the same range, and are found only in B cells, but not in plasma cells. Therefore, in the present invention, for tube A, the three parameters CD19, CD24 and SSC are presented at proper angles so that any plasma cell interference is ruled out, and B-cell gates could be selected with the expression of CD19 and/or CD24 (double positive or either positive), while it could be observed whether an substitute targeted therapy for CD19 ought be selected due to its attenuation or loss before or after the targeted therapy; similarly, in the assay for tube B, the four parameters of CD19, CD72, cCD79a, and SSC are presented at proper angles so that any plasma cell interference is ruled out, and B-cell gates could be selected with the expression of any positive model of three markers (triple positive, double positive or either positive), while it could be observed whether an appropriate targeted therapy ought be selected for the marker CD19 or CD72 according to their separate expression before or after the targeted therapy.

(2) Within the B-cell gates, when the B-cell immunophenotype are observed, a multi-dimensional plot is set up, and it is necessary to select the order and angels according to the characteristics of the expression of each marker during the development of normal B-cells, to prevent the negative and positive results from canceling each other out, which may lower the effectiveness of the multidimensional software. Normal cells are arranged in the best possible way in the order of phase I (T1: CD34pos/CD10bright (bri)/CD38pos/CD81bri/CD20neg/CD45dim), phase II (T2: CD34neg/CD10pos/CD38pos/CD81bri/CD20heterogeneity (het)/CD45pos), and phase III (T3: CD34neg/CD10neg/CD38neg/CD81pos/CD20bri/CD45bri). Also, B-ALL is statistically characterized by CD34pos/CD38dim/CD10bri/CD81dim/CD20neg/CD45 dim, and therefore the regions where MRD tends to occur are kept empty, so that occurrence of any abnormalities, even those not easily detected with two-parameter combinations in a conventional two-dimensional dot plot, can be magnified by a superposition effect, showing a multi-dimensional superposition effect. Within the gate set with multiple markers in multi-dimensions at proper angles, the displayed B-cell development pattern is compared with that of normal cells, and tumor cells are identified with high sensitivity and efficiency.

In some specific embodiments of the present invention, gating is done as follows.

Here, the gates for Tube A are set for flow cytometric detection as follows: a single cell gate P1 is set by using FSC-A/FSC-H, and a live cell gate P2 is set by FSC/SCC, so as to obtain single live cells; different groups of blood cells are gated within the gate P2 by CD45/SSC dot plot; within the gate P2, a CD19pos or CD24pos B cell gate is set with CD19 and CD24, each in combination with SSC. B cell gates are set with a multi-dimensional process with three parameters CD19, CD24, and SSC in combination in three dimensions, and the B cells are observed: given that CD24 is expressed on granulocytes and is therefore not suitable as a CAR-T or other targeted therapeutic marker, the B cell gating for Tube A is relatively simple. It is only necessary to take advantage of the superposition of the two parameters to single out B cells positive for any marker. During the analysis of multi-dimensional graphs, in order to improve the detection sensitivity and avoid any impacts from a weak fluorophore or dim expression on tumor cell and low settings instrument condition that result in difficult to gate, the center of the coordinate axis may be located at a lower left position, with SSC as the vertical axis and CD19 and CD24 as different horizontal axes dividing by a small angle; cell populations positive for any markers is clearly shown and singled out to be set as a B-cell gate, while the presence or absence of CD19 negative cells is also clearly shown. A six-dimensional radar plot of CD45/CD10/CD38/CD20/CD34/CD81 is used within the B-cell gate to display B cells at various stages, with the angle being adjusted so that B cells are distributed in different regions according to various differentiation stage. For example, CD45 is located at an upper middle position (about 345-15 degree), CD20 is located at an upper right position (about 15-45 degree), CD81 is located at an upper left position (about 300-330 degree), CD38 is located at a lower left position (about 210-240 degree), CD34 is located at a lower right position (about 120-150 degree), and CD10 is located at a lower middle position (about 165-195 degree). Therefore, it is possible to position mature B cells of the third stage (T3) at the above position, the earliest primitive cells of the first stage (T1) at the bottom position, and the cells of intermediate stages (T2) run a curve moving from the T1 position firstly to the upper left then to the upper right until it reached the T3 position as the expression of primitive markers CD34, CD10 and CD38 weakened and lost, the expression of mature markers CD20 and CD45 gradually increased, and CD81 with a complicated change. Further, because of the multidimensionality, the cells that are normally aggregated together are spread out, increasing the detection sensitivity. Plasma cells are located in the lower left, with a gap region in the lower right.

Here, the gates for Tube B are set for flow cytometric detection as follows: a single cell gate P1 and a live cell gate P2 are set sequentially; different groups of blood cells are gated within the gate P2 by CD45/SSC dot plot; B cell gates are set with a conventional method by using CD19, CD72 and cytoplasmic CD79a, each in combination with SSC, and B2 cell gates are set with a multi-dimensional analysis method by using a four-parameter four-dimensional radar plot of SSC together with cytoplasmic CD79a, CD19 and CD72. For a maximum sensitivity of B cell detection, the center of the coordinate axis is located at a lower left position, with SSC as the vertical axis and CD19, CD72 and cCD79a as horizontal axes dividing by small angles; cell populations positive for any markers is clearly shown and is gated as B-cells, at the same time the positive or negative expression of CD19 or CD72 is also clearly shown. It is noteworthy that due to the difference in the intensity of expressions of CD19, CD72 and cCD79a themselves, in addition to the brightness of different fluorophores conjugated, and the enhancement of the expression by the superposition of the three markers, with the aim to improve the sensitivity the length of the marker's axis (the distance of the endpoint of the coordinate axis of each marker from the point of origin) should be adjusted according to the rule that the axis length is inversely proportional to the expression intensity, i.e., the endpoint of CD72 axis is the closest to the point of origin for CD72 has the highest expression intensity. A five-dimensional radar plot of CD45/CD10/CD38/CD20/CD34 is used within the B-cell gate to display B cells at various stages, with the angle being adjusted so that B cells are distributed in different regions according to various maturing stage. For example, CD45 is located at an upper left position (about 315-345 degree), CD20 is located at an upper right position (about 30-60 degree), CD38 is located at a lower left position (about 210-240 degree), CD34 is located at a lower right position (about 120-150 degree), and CD10 is located at a lower middle position (about 165-195 degree). Therefore, it is possible to position mature B cells at the third stage (T3) at the above position, the earliest primitive cells at the first stage (T1) at the bottom position, and the cells of intermediate stages (T2) run a curve moving from the T1 position firstly to the upper left then to the upper right until it reached the T3 position as the expression of primitive markers CD34, CD10 and CD38 weakened and lost, the expression of mature markers CD20 and CD45 gradually increased. Further, because of the multidimensionality, the cells that overlayed in traditional dot plot may spread out, increasing the detection sensitivity. Plasma cells are located in the lower left. The lower right region is blank for normal specimen, which means that cells in this region are highly suspected as malignant. Within the gate P2, gating is done with a three-dimensional radar plot of three antibodies, cCD79a, CD19, and CD72, allowing the evaluation of CD19 and CD72 expression on tumor cells as well as the selection of appropriate targeted therapeutic regimens. The angles are adjusted so that the cCD79a marker is the longitudinal axis which centered at the horizontal axis, and CD72 and CD19 located on either side of the horizontal axis at small angles (e.g., CD19 at 315-345 degree and CD72 at 15-45 degree, their positions at the left or right are interchangeable). Further, in order to improve the detection sensitivity and avoid any impacts from a weak fluorophore or dim expression of tumor cells and low settings instrument condition that result in difficulty in gating, the horizontal coordinate axis may be located at the bottom position, and cCD79a$^+$/CD72$^+$/CD19$^-$ cells and cCD79a$^+$/CD72$^-$/CD19$^+$ cells are singled out, respectively. In normal circumstances, the ratio of cCD79a$^+$/CD72$^+$/CD19$^-$ cells is extremely low, and cCD79a+/CD72-/CD19+ cells are plasma cells. In case of tumors, B-cell developmental expression pattern analysis is done for validation, so as to find whether CD19 and/or CD72 are expressed on tumor cells, thereby selecting an appropriate regimen for further targeted therapy.

Any appearance of a development pattern different from the normal could be suspected as malignant, and a positive MRD is diagnosed after excluding the influence of other factors.

According to another aspect of the present invention, the inventor has also discovered in the study that CD72 could be used not only as an efficient B-cell gating marker for the flow cytometry of B-cell tumors after targeted therapy according to the present invention, but also as a promising new target for the treatment of malignant tumors, especially B-cell tumors. In a plurality of samples tested by the inventor from October 2020 to August 2021, after extensive research and repeated testing and analysis, it was found that CD72, a marker with sensitivity, specificity, and expression intensity as good as CD19, can be used both as a post-targeted therapy gating marker and as a promising breakthrough target for malignant tumors, especially B-cell tumors, after CD19. In the study of the present invention, it was found that CD72 was 97.73% positive in B-cell acute lymphoblastic leukemia (B-ALL), and that CD72 had higher specificity than CD19 and was not expressed in either normal or malignant plasma cells. CD72 expression rates in other diseases were 100% for B-lineage mature lymphocytic neoplasms (including Burkitt's lymphoma (burkitt), chronic lymphocytic leukemia (CLL), diffuse large B-cell lymphoma (DLBCL), follicular lymphoma (FL), hairy cell leukemia (HCL), lymphoplasmacytic lymphoma (LPL), mantle cell lymphoma (MCL), marginal zone lymphoma (MZL), and small cell lymphoma (SLL)), 14.29% for T-cell acute lymphoblastic leukemia (T-ALL), 40% for mixed-phenotype acute leukemia (MPAL, but 100% on malignant cells involved B immunephenotype), and 10.85% for acute myeloid leukemia (AML). Therefore, CD72 can be used as a therapeutic target for screening or manufacturing immunotherapys for the treatment of B-cell acute lymphoblastic leukemia, B-lineage mature lymphocytic neoplasms, even for other malignant tumors expression CD72, for example, T-cell acute lymphoblastic leukemia, mixed-phenotype acute leukemia, and acute myeloid leukemia . . . CD72 can be used as a target alone, or in combination with other markers such as CD19 and/or CD22, BAFFR, and the like. The malignant tumor can be a tumor not subjected to targeted therapy, or a recurrent tumor after targeted therapy (e.g., after targeted therapy such as those with CD19, CD22, BAFFR, and/or CD72 of the present invention). In the present invention, CD72 is used as a target for the treatment (including adjuvant treatment) of the malignant tumors and can be used as an alternative for B-ALL and B-cell lymphomas in the case where CD19 is weakly expressed or lost after CD19-CAR-T or other targeted therapy, which is particularly significant for cases in which B-cell markers such as CD19 and/or CD22 or even BAFFR may be dim or lost after targeted therapy with these B-cell markers.

Thus, the present invention also provides the use of CD72 as a target in the screening and/or manufacture of an immunetherapy for treating malignancies, wherein the malignancies comprise B-cell acute lymphoblastic leukemia, B-lineage mature lymphocytic tumors, T-cell acute lymphoblastic leukemia, mixed phenotype acute leukemia, or acute myeloid leukemia. Specifically, the CD72 is the membrane CD72, preferably the cell membrane protein CD72 of the bone marrow or peripheral blood of an individual.

According to a specific embodiment of the present invention, for the use of CD72 as a target in the screening and/or manufacture of an immunetherapy for treating B-cell tumors, the B-lineage mature lymphocytic tumors comprise Burkitt's lymphoma, chronic lymphocytic leukemia, diffuse large B-cell lymphoma, follicular lymphoma, hairy cell leukemia, lymphoplasmacytic lymphoma, mantle cell lymphoma, marginal zone lymphoma, or small cell lymphoma.

According to a specific embodiment of the present invention, for the use of CD72 as a target in the screening and/or manufacture of an immunetherapy for treating malignant tumors, the CD72 is used as a target alone or in combination with other markers such as CD19, CD22 and/or BAFFR.

According to a specific embodiment of the present invention, for the use of CD72 as a target in the screening and/or manufacture of an immunetherapy for treating malignant tumors, the malignant tumor is either a tumor not subjected to targeted therapy or a recurrent tumor after targeted therapy (e.g., after targeted therapy such as those with CD19, CD22, BAFFR, and/or CD72 of the present invention).

In some specific embodiments, the malignant tumor is a B-lineage mature lymphocytic tumor that has not been treated with targeted therapy. In some another specific embodiments, the malignant tumor is a B-lineage mature lymphocytic tumor that has relapsed after targeted therapy. In some more specific embodiments, the malignant tumor is a CD72-positive B-cell acute lymphoblastic leukemia, T-cell acute lymphoblastic leukemia, mixed phenotype acute leukemia, or acute myeloid leukemia, which has not been treated with targeted therapy. In some another more specific embodiments, the malignant tumor is CD72-positive B-cell acute lymphoblastic leukemia, T-cell acute lymphoblastic leukemia, mixed phenotype acute leukemia, or acute myeloid leukemia, which has relapsed after targeted therapy.

In some more specific embodiments, the malignant tumor is a tumor in which the CD19, CD22 and/or BAFFR markers are dim or lost after targeted therapy. For patients with such a tumor, the present invention provides CD72 as an effective target.

In summary, the present invention provides a flow cytometric detection reagent composition and use thereof for B-cell tumors after targeted therapy. The advantages of the present invention include: (1) maximally preventing missed diagnosis due to loss or dim expression of B-cell markers after primary or targeted therapy; (2) simultaneously performing three-parameter three-dimensional analysis of the B-cell markers CD19, cCD79a, and CD72, which can accurately assess promising B-lineage expression markers as targets for targeted therapy of B-lineage tumors while detecting MRD, and provide experimental evidences for the selection of an appropriate targeted therapy for patients; (3) multi-parameter and multi-dimensional setting of B-cell gating and analyzing the expression of B cells at various stages, and simplifying by shrinking dozens of pictures into a few, thereby improving the efficiency and decreasing the rate of missed diagnosis, which is suitable for both the current manual analysis and provides a prototype for the development of artificial intelligence for FCM softwares; (4) maximally ensuring clinical utility of the present invention, and increasing the sensitivity and specificity to nearly 100% with the method according to the invention, in comparison to a combinational approach for B-ALL MRD detection by using a 8-color flow cytometer with the highest clinical coverage at present where a coverage of 80-95% cases is achieved for MRD observation with CD45/CD10/CD38/CD20/CD34 and a coverage of 90-97% cases with CD45/CD10/CD38/CD20/CD34/CD81; and (5) providing a B-cell gating marker, the antibody CD72, which has high efficiency after B-targeted therapy and is expected to serve as a new target for the treatment of B-cell tumors in addition to CD19.

BRIEF DESCRIPTION OF THE DRAWINGS

FIGS. 1A to 1D and FIG. 2 show the results of flow cytometric gating analysis of the same normal bone marrow sample according to a specific embodiment of the present invention, wherein:

FIGS. 1A to 1D show the normal bone marrow sample analyzed with CD19/SSC gating in tubes A and B, CD24/SSC gating in tube A, CD72/SSC gating in tube B, and cCD79a/SSC gating in tube B, respectively, followed by observation of the two-dimensional dot plots generated by CD45/CD10/CD38/CD20/CD34/CD81 or CD45/CD10/CD38/CD20/CD34 in two-by-two combinations within the B cell gates set by each B cell marker.

FIG. 2 shows the multi-parameter multi-dimensional analysis in both tubes A and B with the same normal bone marrow sample as presented in FIGS. 1A to 1D.

FIGS. 3A to 3D and FIG. 4 show the results of flow cytometric gating analysis of a bone marrow sample from the same MRD$^+$ B-ALL patient after CD19 CAR-T therapy according to a specific embodiment of the present invention, wherein:

FIGS. 3A to 3D show the bone marrow sample from a B-ALL patient with MRD$^+$ after CD19 CAR-T therapy, analyzed with CD19/SSC gating in tubes A and B, CD24/SSC gating in tube A, CD72/SSC gating in tube B, and cCD79a/SSC gating in tube B, respectively, followed by observation of the two-dimensional dot plots generated by CD45/CD10/CD38/CD20/CD34/CD81 or CD45/CD10/CD38/CD20/CD34 in two-by-two combinations within the B cell gates set by each B cell marker.

FIG. 4 shows the multi-parameter multi-dimensional analysis in both tubes A and B with the same bone marrow sample of the B-ALL patient with MRD$^+$ after CD19 CAR-T therapy as shown in FIGS. 3A to 3D.

DETAILED DESCRIPTION OF THE INVENTION

Figure 1A:
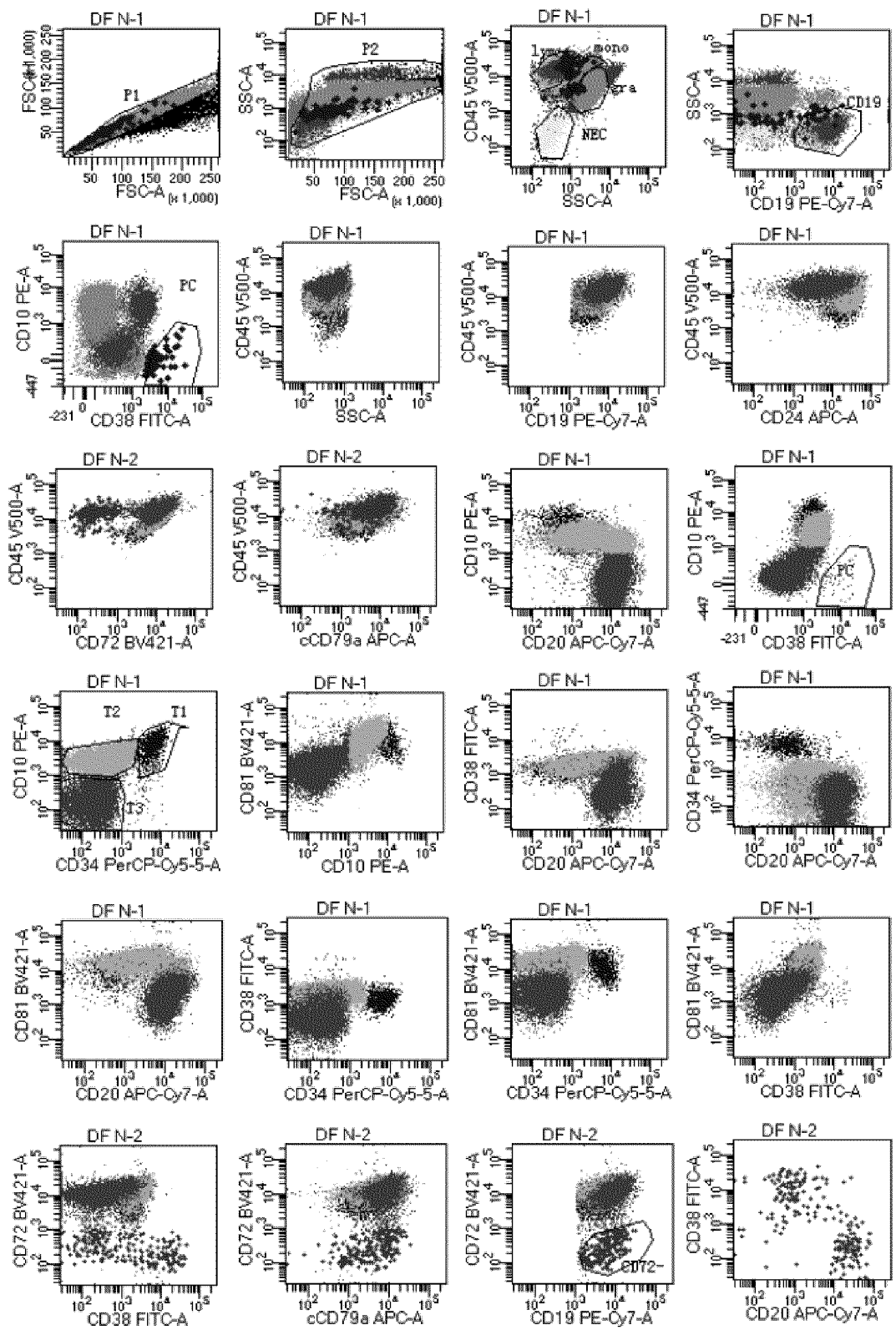

For better understanding of the technical features, objects and advantageous effects of the present invention, the technical solutions of the present invention are hereinafter described in details, which is not to be construed as limitation to the implementable scope of the present invention.

Example 1. Preparation of Reagents

The antibody combination used in this example includes:
a first group of antibodies of: anti-CD38 antibody, anti-CD10 antibody, anti-CD34 antibody, anti-CD19 antibody, anti-CD24 antibody, anti-CD20 antibody, anti-CD81 antibody, anti-CD45 antibody, each being labeled with fluorescence, in this order, FITC, PE, PerCP-Cy5.5, PE-Cy7, APC, APC-Cy7, BV421, and V500, respectively, wherein the above eight monoclonal antibody reagents were mixed and accommodated in a first container in a volume ratio of 5:5:5:3:2:3:3:3;
a second group of antibodies of: anti-CD38 antibody, anti-CD10 antibody, anti-CD34 antibody, anti-CD19 antibody, anti-CD20 antibody, anti-CD72 antibody, and anti-CD45 antibody, each being labeled with fluorescence, in this order, FITC, PE, PerCP-Cy5.5, PE-Cy7, APC-Cy7, BV421, and V500, respectively, wherein the above seven monoclonal antibody reagents were mixed and accommodated in a second container in a volume ratio of 5:5:5:3:3:3:3; and a third group of antibodies of cytoplasmic (c) CD79a-APC accommodated in a third container.

The antibodies in this example were commercially available, among which cCD79a-APC was a product of 4A Biotech Co., Ltd (made in China), and the rest of the direct fluorescent-labeled antibodies were products of Becton Dickinson, USA.

Optionally, lysing solution was prepared in a fourth container, solution A of a permeabilization reagent in a fifth container, solution B of a permeabilization reagent in a sixth container, and a PBS buffer in a seventh container. The lysing solution, permeabilization reagent, and PBS buffer were commercially available, among which the lysing solution and the permeabilization reagent were both from Becton Dickinson, USA, and the PBS buffer was from Beckman Coulter, Inc.

Example 2. Sample Processing

According to the cell counting results, the bone marrow or peripheral blood samples anti-coagulated by heparin or EDTA were added to the flow cytometric Tube A to ensure that the amount of cells added was about $2 \times 10^6$. Then, 29 µl of each of the eight different fluorescent-labeled monoclonal antibody reagents were added to the flow cytometric tube according to Table 1, mixed thoroughly with the cell suspension and incubated for 15 minutes at room temperature in dark. 3 ml of 1× lysing solution was added and incubated for 10 minutes in dark to lyse erythrocytes, and centrifuged at 1500 rpm for 5 minutes before the supernatant was removed, followed by washing with 3 ml PBS buffer and centrifugation to remove the supernatant. The cells were resuspended with 0.5 ml PBS buffer, and the processed sample was ready for detection.

TABLE 1

Antibody combinations and usage in tubes A and B

| Fluorophores | Tube A First container | Usage (µl) | Tube B Second container | Third container | Usage (µl) |
|---|---|---|---|---|---|
| FITC | CD38 | 5 | CD38 | \ | 5 |
| PE | CD10 | 5 | CD10 | \ | 5 |
| PerCP-Cy5.5 | CD34 | 5 | CD34 | \ | 5 |
| PE-CY7 | CD19 | 3 | CD19 | \ | 3 |
| APC | CD24 | 2 | \ | cCD79a | 2 |
| APC-Cy7 | CD20 | 3 | CD20 | \ | 3 |
| BV421 | CD81 | 3 | CD72 | \ | 3 |
| V500 | CD45 | 3 | CD45 | \ | 3 |

According to the cell counting results, the bone marrow or peripheral blood samples anti-coagulated by heparin or EDTA were added to the flow cytometric Tube B to ensure that the amount of cells added was about $2 \times 10^6$. Then, 29 µl of each of the seven different fluorescent-labeled monoclonal antibody reagents were added to the flow cytometric tube according to Table 1, mixed thoroughly with the cell suspension and incubated for 15 minutes at room temperature in dark. 100 µl of Solution A was added and incubated for 5 minutes in dark, 3 ml of 1× lysing solution was added and incubated for 10 minutes in dark to lyse erythrocytes, and centrifuged at 1500 rpm for 5 minutes before the supernatant was removed, and then 50 µl of Solution B and 2 µl of the cytoplasmic monoclonal antibody reagent cCD79a-APC was added and incubated for 15 minutes in dark. 3 ml PBS buffer was finally added for washing, and centrifugation was carried out to remove the supernatant. The cells were resuspended with 0.5 ml PBS buffer, and the processed sample was ready for detection.

Example 3. Sample Testing

The samples processed according to the method of Example 2 were tested on a flow cytometer of the Becton Dickinson 3-laser 8-color FACS Canto II model or similar instrument. Preferably, after obtaining 1,000,000 cells per tube (at least 300,000 as recommended), the data were analyzed using the diva 2.8 software and other softwares such as kaluza.

Here, for the flow cytometric detection, gating were set as follows.

(1) conventional gating: a single cell gate P1 was set by FSC-A/H, and a live cell gate P2 set by FSC/SSC sequentially; within the gate P2, some major blood cell gates was set with CD45/SSC. (2) CD19 and CD24 were respectively used in combination with SSC to set the B cell gates for tube A, and CD19, CD72, cCD79a were respectively used in combination with SSC to set the B cell gates for tube B. (3) Gating with multi-dimensional parameters: CD19 and CD24 were used in combination with SSC to set a three-parameter three-dimensional B-cell gate B1 for tube A; for tube B, CD19, CD72, cCD79a were used in combination with SSC to set a four-parameter four-dimensional B-cell gate B2, and a three-parameter three-dimensional radar plot was set by CD19, CD72, and cCD79a to achieve the CD19neg B-cell gate and the CD72neg B-cell gate. (4) CD38/CD34/CD10/CD20/CD81/CD45 for Tube A and CD38/CD34/CD10/CD20/CD45 for Tube B were used in two-by-two combinations to show the expression of cells within each B-cell gate. (5) Multi-dimensional analysis: within the B1 cell gate, a six-parameter six-dimensional plot was generated with CD38/CD34/CD10/CD20/CD81/CD45 in Tube A to observe B-cell maturing; within the B2 cell gate, a five-parameter five-dimensional plot was generated with CD38/CD34/CD10/CD20/CD45 observe B-cell maturing; for CD72neg or CD19neg B cells, the five-parameter five-dimensional plots of both cell populations were analyzed simultaneously.

There was a variable proportion of normal proliferating B progenitor cells (hematogones) in normal bone marrow, and these hematogones can increase significantly in proportion after chemotherapy or when stimulated by other factors, which may interfere with MRD determination (FIG. 1A to FIG. 1D, and FIG. 2).

The combination of markers of the present invention allows precisely targeting of the target cells.

Figure 1B:
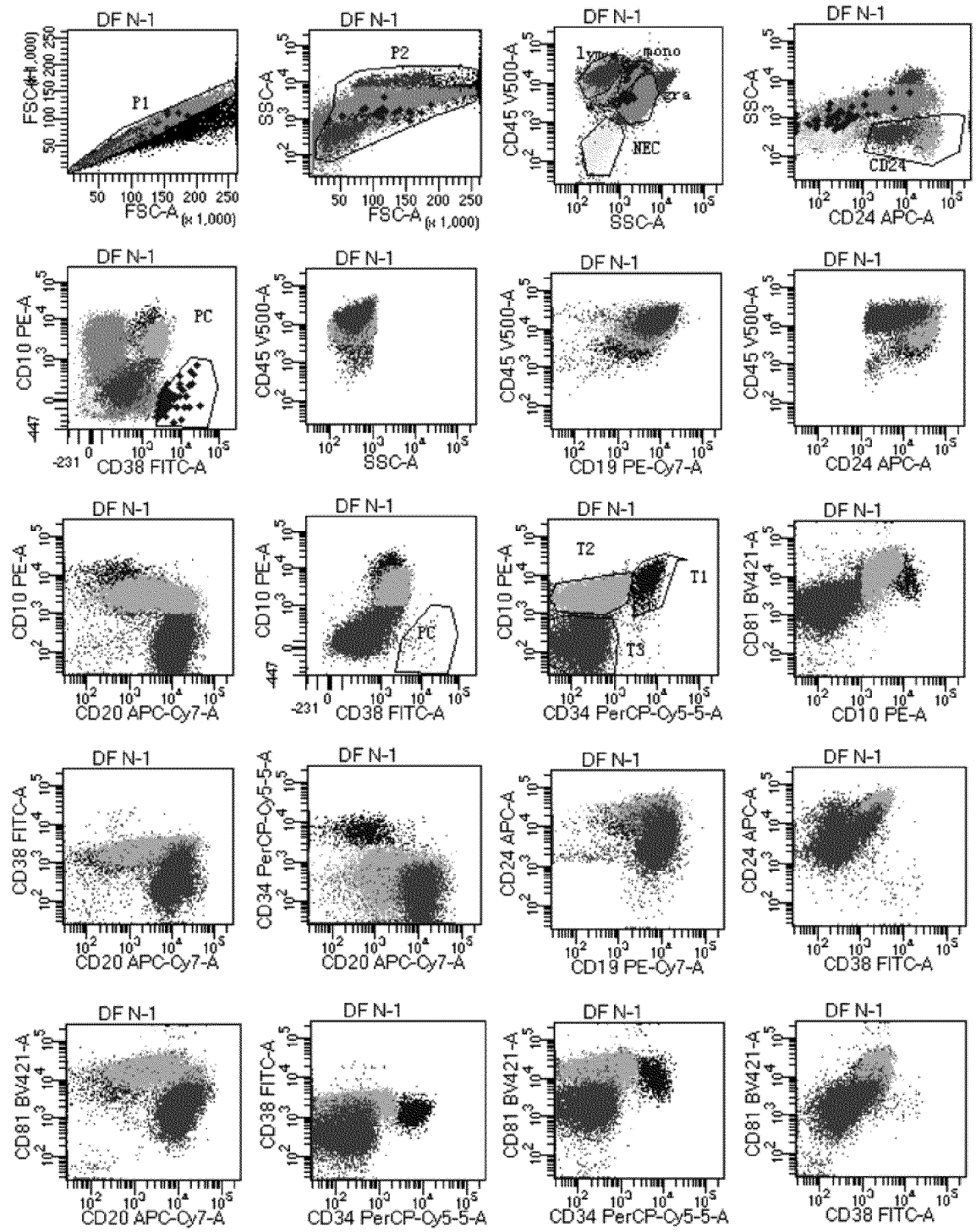
Figure 1C:
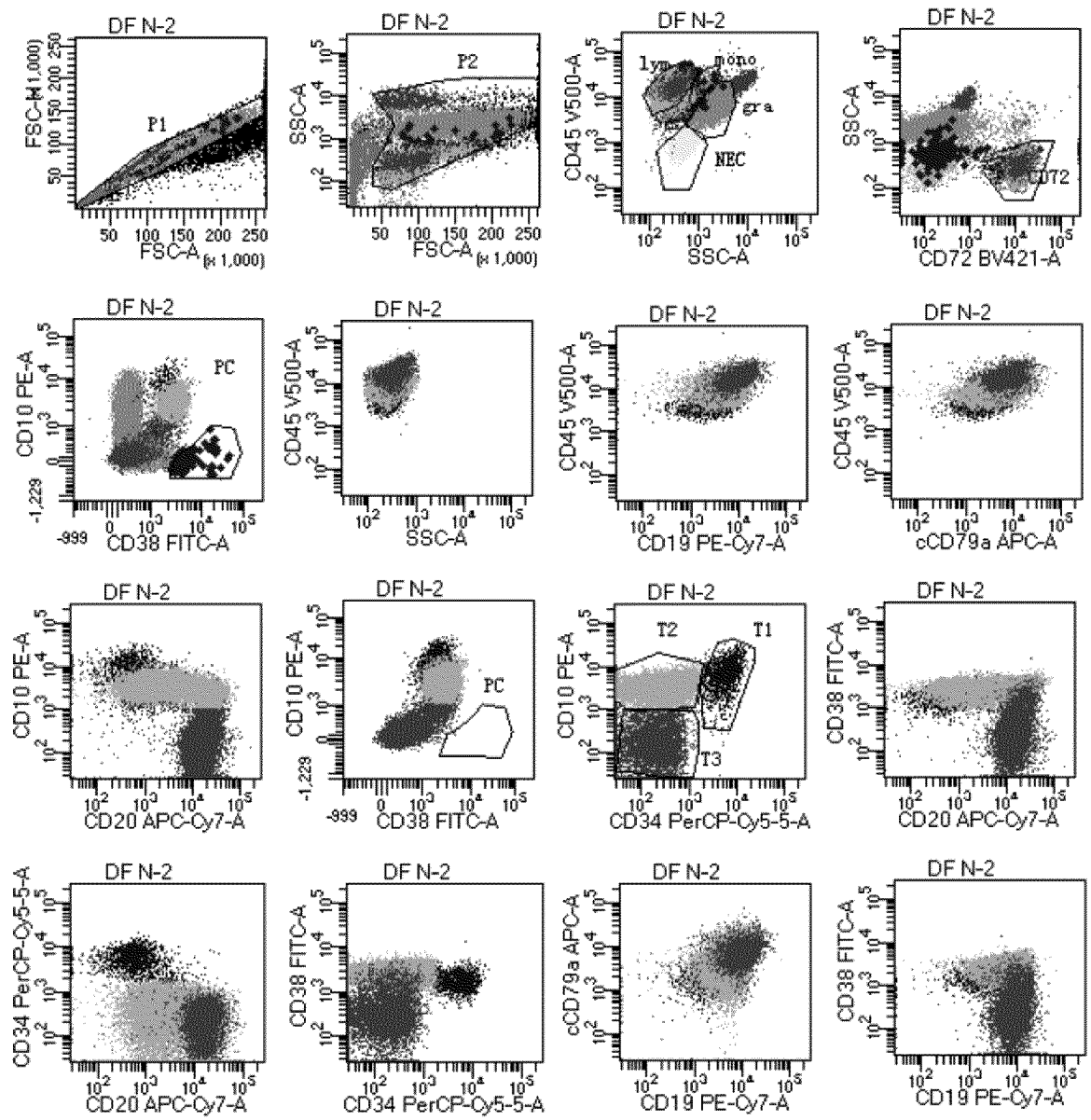
Figure 1D:
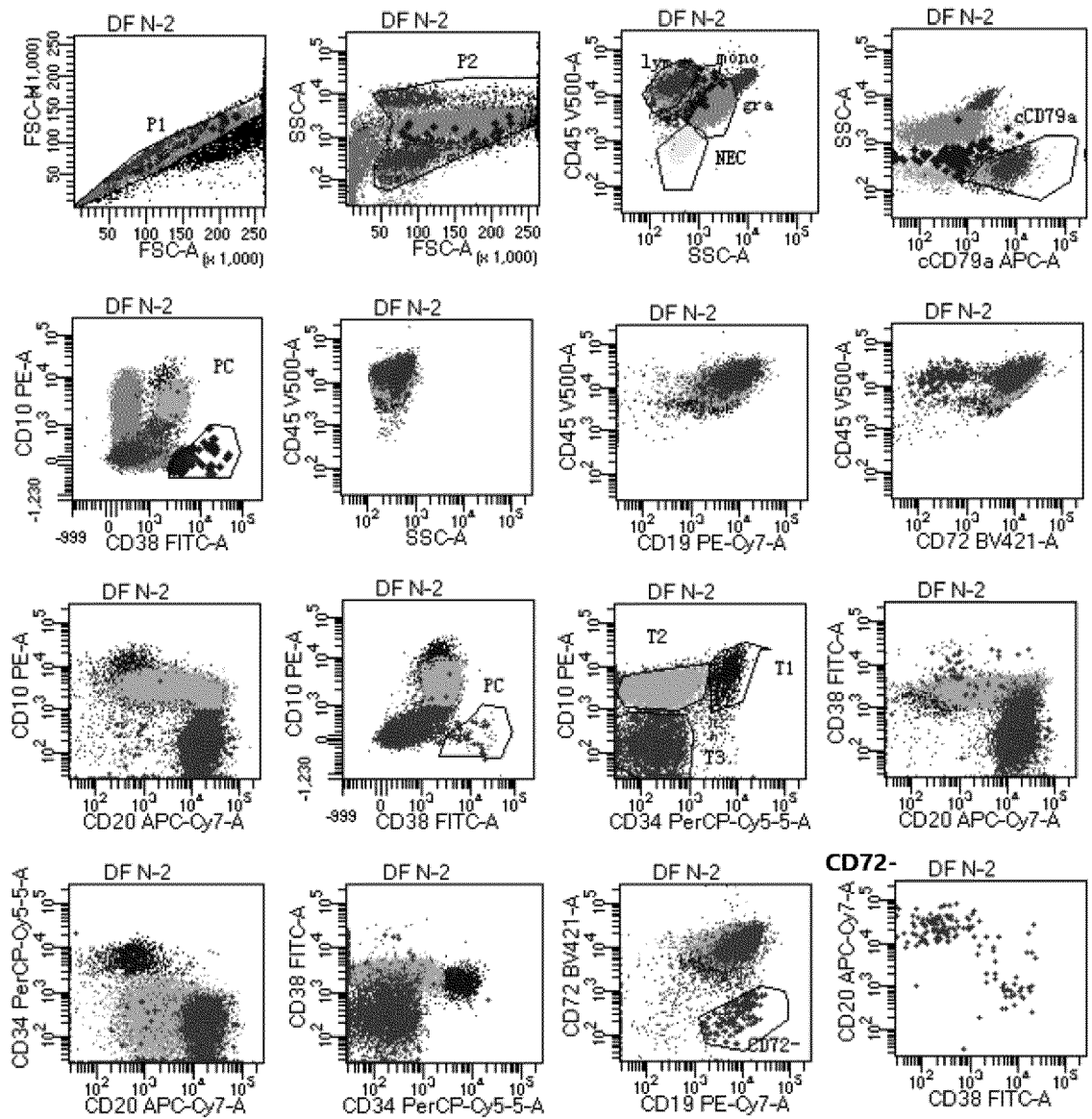

Normal CD19neg B cells have different expression from that of common CD19pos B cells, the CD19neg population is mostly the earliest stage B progenitor cells that show diminished CD10 expression and high SSC and are very easily misdiagnosed as ALL-B MRD (FIG. 1B to FIG. 1D). This cell population is present in normal circumstances, but is always overlooked because of its extremely low proportion in most cases and the fact that CD19 is currently the only applied marker to set B cell gate in most cases. The method with multi-marker combination for B-cell gating of the present invention, as well as the multi-parameter multi-dimensional image analysis method can make this cell population visible.

In this example, 20 normal bone marrow samples were first selected for assaying. All normal bone marrow B cells, though having different proportions and different percentages of B cells at each stage of maturing, showed a regular pattern of differentiation in terms of antigen appearance time, expression intensity and the two-by-two combinations (FIG. 1A to FIG. 1D, and FIG. 2), divided into 3 stages where CD19neg B cells may be present in some stages. Five- and six-dimensional software analysis done simultaneously could have a superposition effect to enhance sensitivity, and with the graphs of five or six parameters of normal B cells presented in one plot. Based on this, tumor cells showed a difference more or less from normal cells in terms of the expression pattern of various antigens and antigen combinations, an MRD positive was then determined by this difference (0.01% as cut off value), and a proportion of malignant cells exceeding 5% of the nucleated cells was considered a relapse.

This example illustrates one normal case and one relapse case after B-ALL CD19-CAR-T. FIG. 1A to FIG. 1D and FIG. 2 show a normal sample. (1) a single cell gate P1, a live cell gate P2, and a CD45/SSC blood cell gate was routinely set. (2) Within the gate P2, for tube A, CD19 and CD24 were used respectively in combination with SSC to set a B-cell gate, and for tube B, CD19, CD72 and cCD79a were used respectively in combination with SSC to set respective B-cell gates, and the two-dimensional dot plots of two-by-two combinations of CD38/CD34/CD10/CD20/CD81/CD45 in Tube A and two-by-two combinations of CD38/CD34/CD10/CD20/CD45 in Tube B were analyzed separately to show the developmental expression patterns of normal B cells from early to mature stages. (3) Gating with multi-dimensional parameters: CD19 and CD24 were used in combination with SSC to set a three-parameter three-dimensional B-cell gate B1 for tube A; for tube B, CD19, CD72, cCD79a were used in combination with SSC to set a four-parameter four-dimensional B-cell gate B2, and a three-parameter three-dimensional radar plot was set by CD19, CD72, and cCD79a to achieve the CD19neg B-cell gate and the CD72neg B-cell gate. (4) Multi-dimensional analysis: within the B1 cell gate, a six-parameter six-dimensional plot was generated with CD38/CD34/CD10/CD20/CD81/CD45 in Tube A to observe B-cell maturing; within the B2 cell gate, a five-parameter five-dimensional plot was generated with CD38/CD34/CD10/CD20/CD45 observe B-cell maturing; in order to show the relationship more clearly among the B cell markers, within the gate B2 of tube B, a three-parameter three-dimensional radar plot was set by CD19, CD72, and cCD79a to observe the CD19neg B-cells and the CD72neg B-cells, while the five-parameter five-dimensional plots of CD38/CD34/CD10/CD20/CD45 in CD19neg and CD72neg populations were analyzed simultaneously.

Specifically, FIGS. 1A to 1D all showed the normal bone marrow sample analyzed with CD19/SSC gating for tubes A and B, CD24/SSC gating for tube A, CD72/SSC gating for tube B, and cCD79a/SSC gating for tube B, respectively, followed by observation of the two-dimensional dot plots generated by CD45/CD10/CD38/CD20/CD34/CD81 or CD45/CD10/CD38/CD20/CD34 in two-by-two combinations within the B cell gates set by each B cell marker, and observation of normal expression pattern of B cells at various maturing stages (from the earliest T1 stage of $CD34^+$ $CD10'$, the T2 stage of $CD34^-$ $CD10^+$, to the T3 stage of $CD34^-$ $CD10"$). CD72 and CD24 were only present on B cells, and were not expressed by plasma cells. CD19 and cCD79a were expressed by both normal B cells and plasma cells. CD19 gating and cCD79a gating showed a small number of CD72 negative cells in the normal sample, all being plasma cells or $CD20'$ mature B cells, which had no impact on the role of CD72 as a B-ALL MRD detection marker and a promising target for CAR-T treatment of B-ALL.

Figure 2:
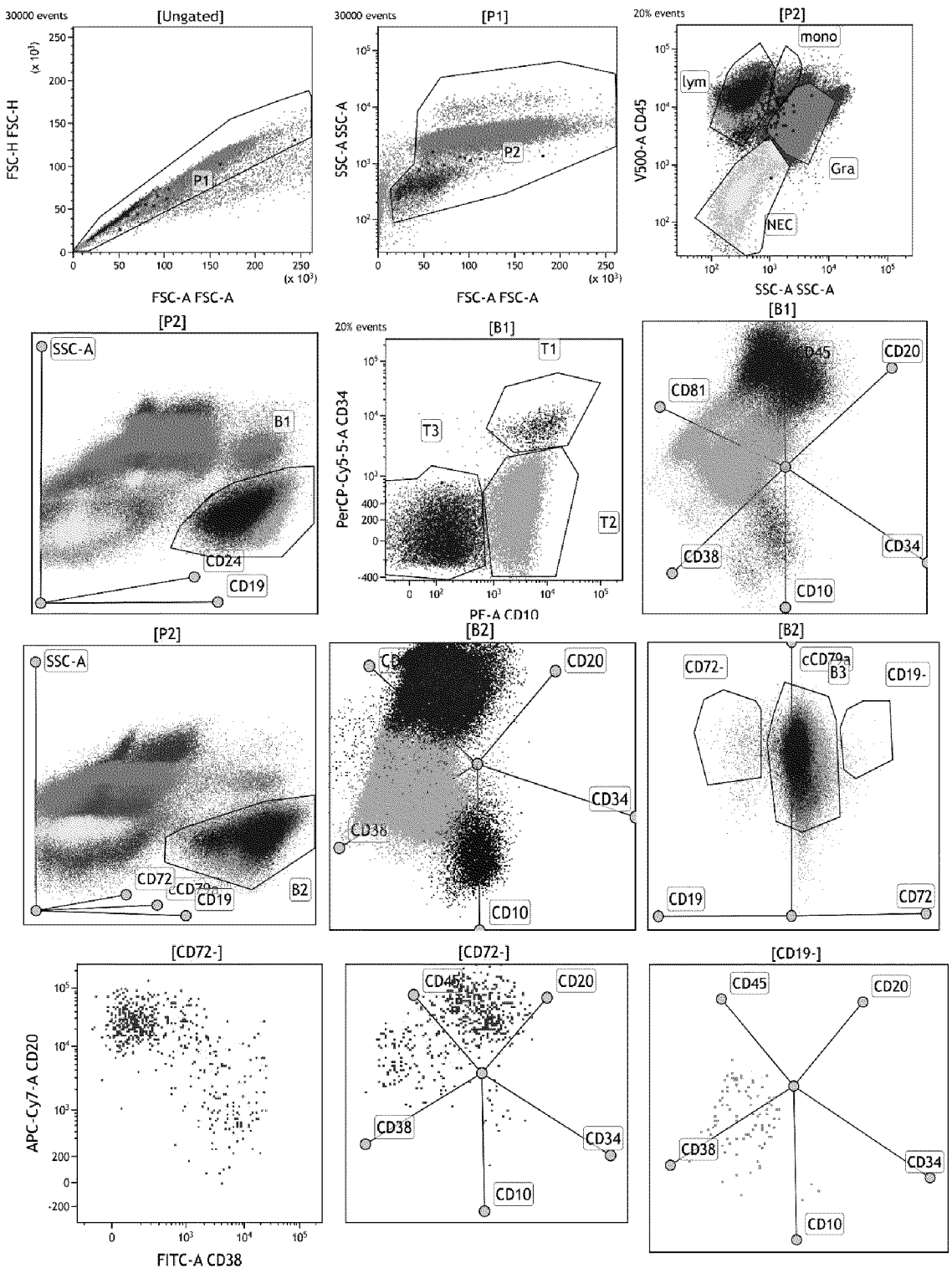
Figure 3A:
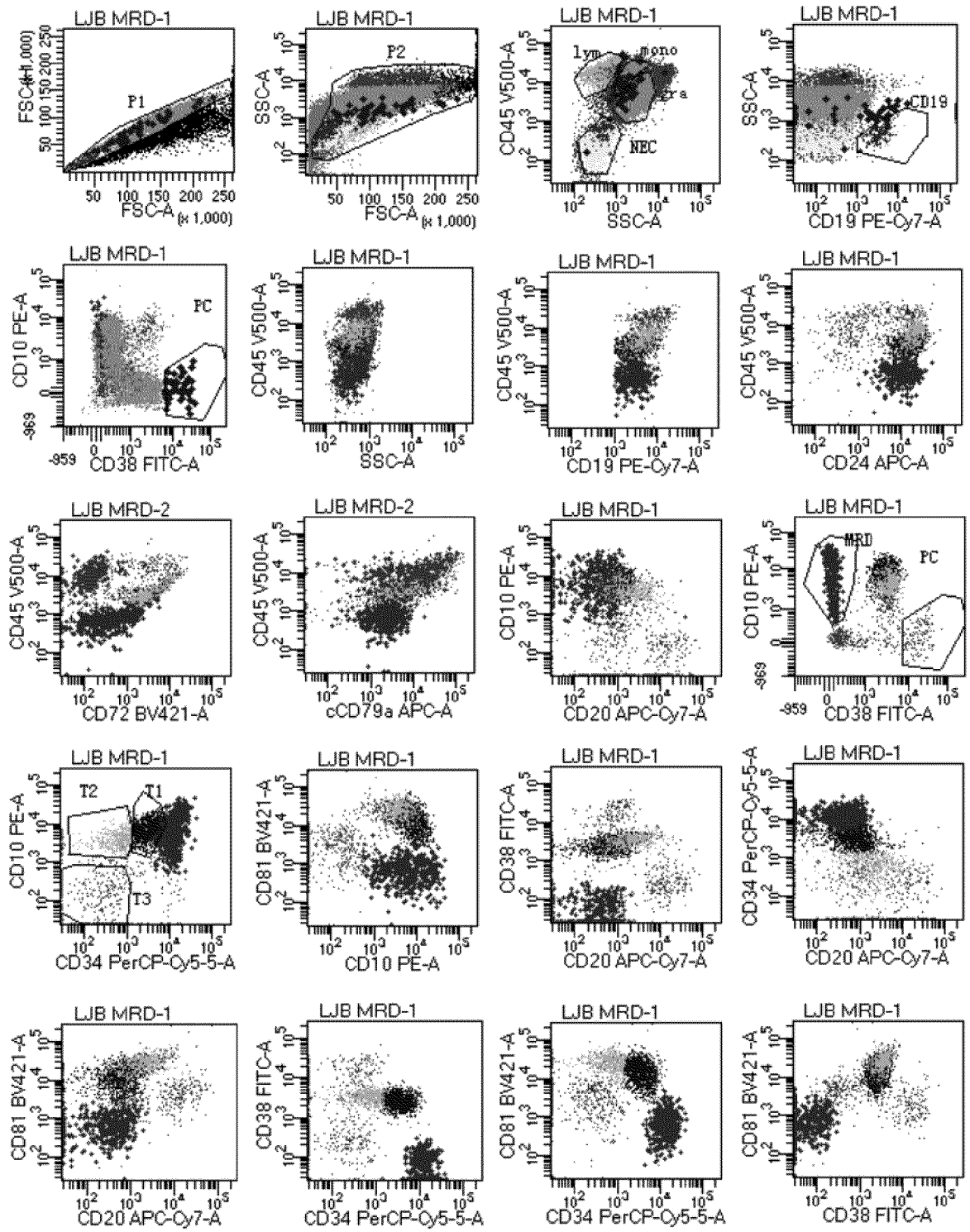
Figure 3B:
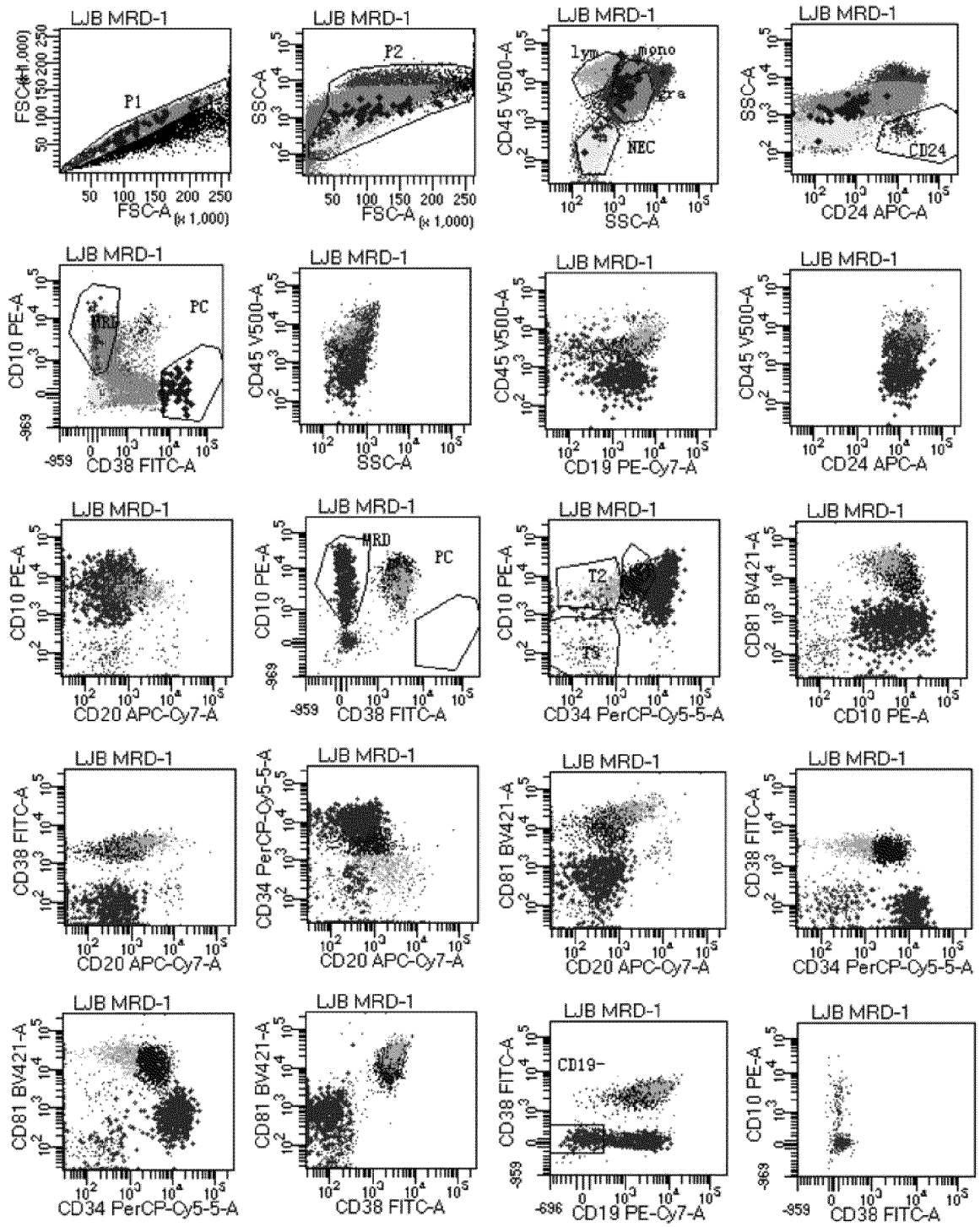
Figure 3C:
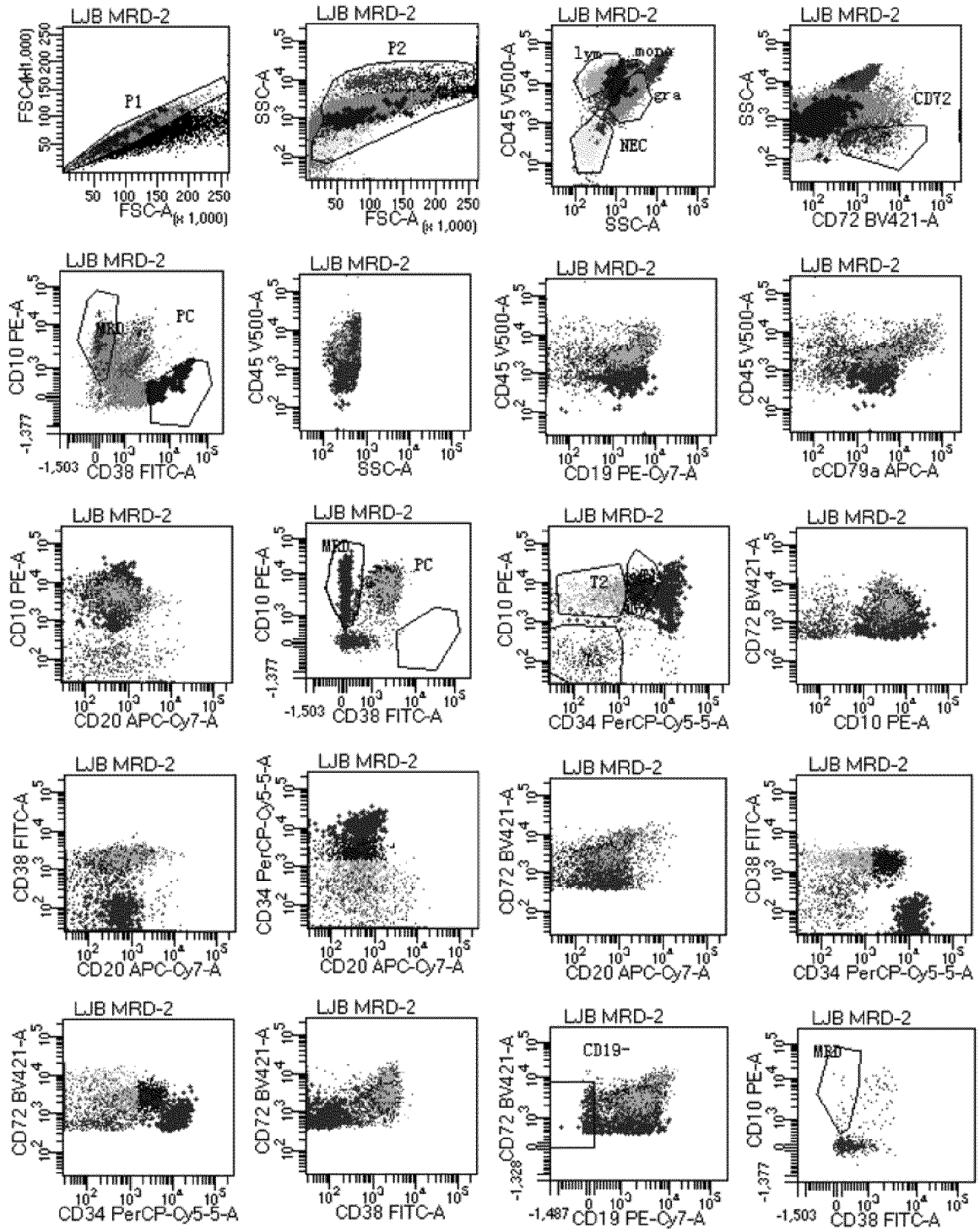
Figure 3D:
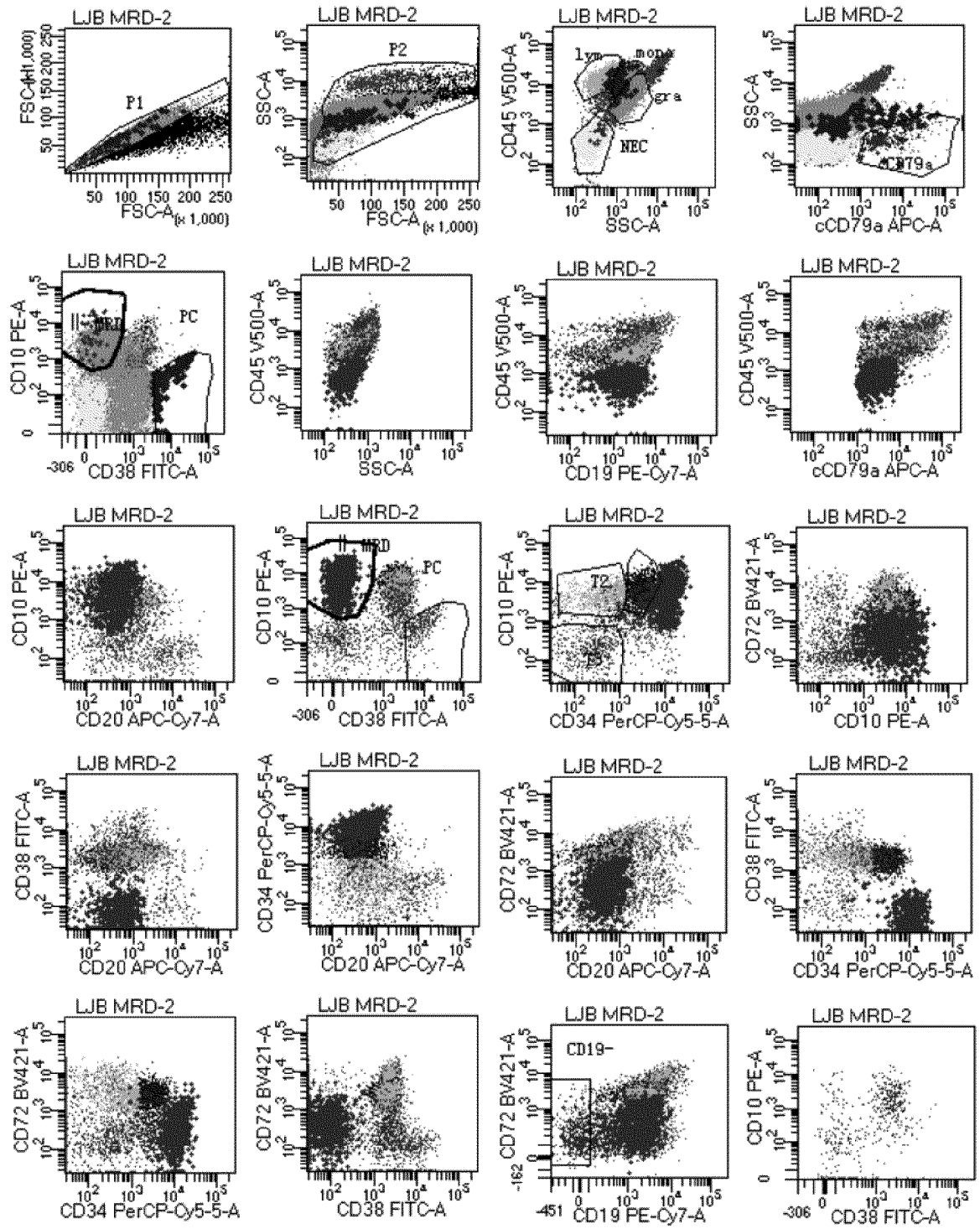

Specifically, FIG. 2 showed the multi-parameter multi-dimensional analysis in both tubes A and B with the same normal bone marrow sample as presented in FIGS. 1A to 1D. Tube A analysis: a single cell gate P1 and a live cell gate P2 gate were orderly set, and then a three-parameter three-dimensional radar plot was set by CD19, CD24 and SSC to achieve a B1 cell gate within the gate P2 for tube A. Within the B1 cell gate, normal B cells were divided into T1 ($CD34^+$ CD101, T2 ($CD34^-$ $CD10^+$), and T3 ($CD34^-$ CD10) cells at three different maturation stages by using the CD34/CD10 two-dimensional dot plot. The CD38/CD10/CD34/CD20/CD45/CD81 six-parameter six-dimensional radar plot was used to observe the normal B cell development process, with the angles adjusted so that normal B cells were respectively in the T1, T2, and T3 stages from bottom to top on the left side while the right side was kept empty as regions of high MRD occurrence. Tube B analysis: a single cell gate P1 and a live cell gate P2 gate were orderly set, and a four-parameter four-dimensional radar plot was set by CD19, CD72, cCD79a and SSC to achieve the B2 cell gate within the gate P2. Within the B2 cell gate, a five-parameter five-dimensional radar plot of CD38/CD10/CD34/CD20/CD45 was used for the observation of normal B-cell maturation. Similarly to that with tube A, the angles were adjusted so that normal B cells were respectively in the T1, T2, and T3 stages from bottom to top on the left side while the right side was kept empty as regions of high MRD occurrence. Within the gate B2, a three-parameter three-dimensional radar plot was set using CD19, CD72, and cCD79a to detect CD19neg or CD72neg cell populations. A small number of CD72neg cell populations were plasma cells or CD20bright mature B cells. A small number of CD19neg cell populations were early-stage cells. FIG. 1A to FIG. 1D includes dozens of complex two-dimensional dot plots, while FIG. 2 clearly shows the mutual relationships with only 9 to 12 plots.

FIGS. 3A to 3D, and FIG. 4 show the results of flow cytometric gating analysis of a bone marrow sample from the same MRD positive B-ALL patient after CD19 CAR-T therapy according to a specific embodiment of the present invention.

Specifically, FIGS. 3A to 3D show the bone marrow sample from a B-ALL patient with MRDpositive after CD19 CAR-T therapy, analyzed with CD19/SSC gating in tubes A and B, CD24/SSC gating in tube A, CD72/SSC gating in tube B, and cCD79a/SSC gating in tube B, respectively, followed by observation of the two-dimensional dot plots generated by CD45/CD10/CD38/CD20/CD34/CD81 or CD45/CD10/CD38/CD20/CD34 in two-by-two combinations within the B cell gates set by each B cell marker. FIG. 1A to FIG. 1D were used as controls to see if there were cells with different developmental patterns and expressions from the normal ones. It can be seen that MRD cells with $CD38^-$ $CD10^+$ $CD81^{dim}CD34^+$ $CD20^-$ $CD45^{dim}$were positive for cCD79a, CD24, CD72, and mostly CD19pos with a small CD19neg subset.

Figure 4:
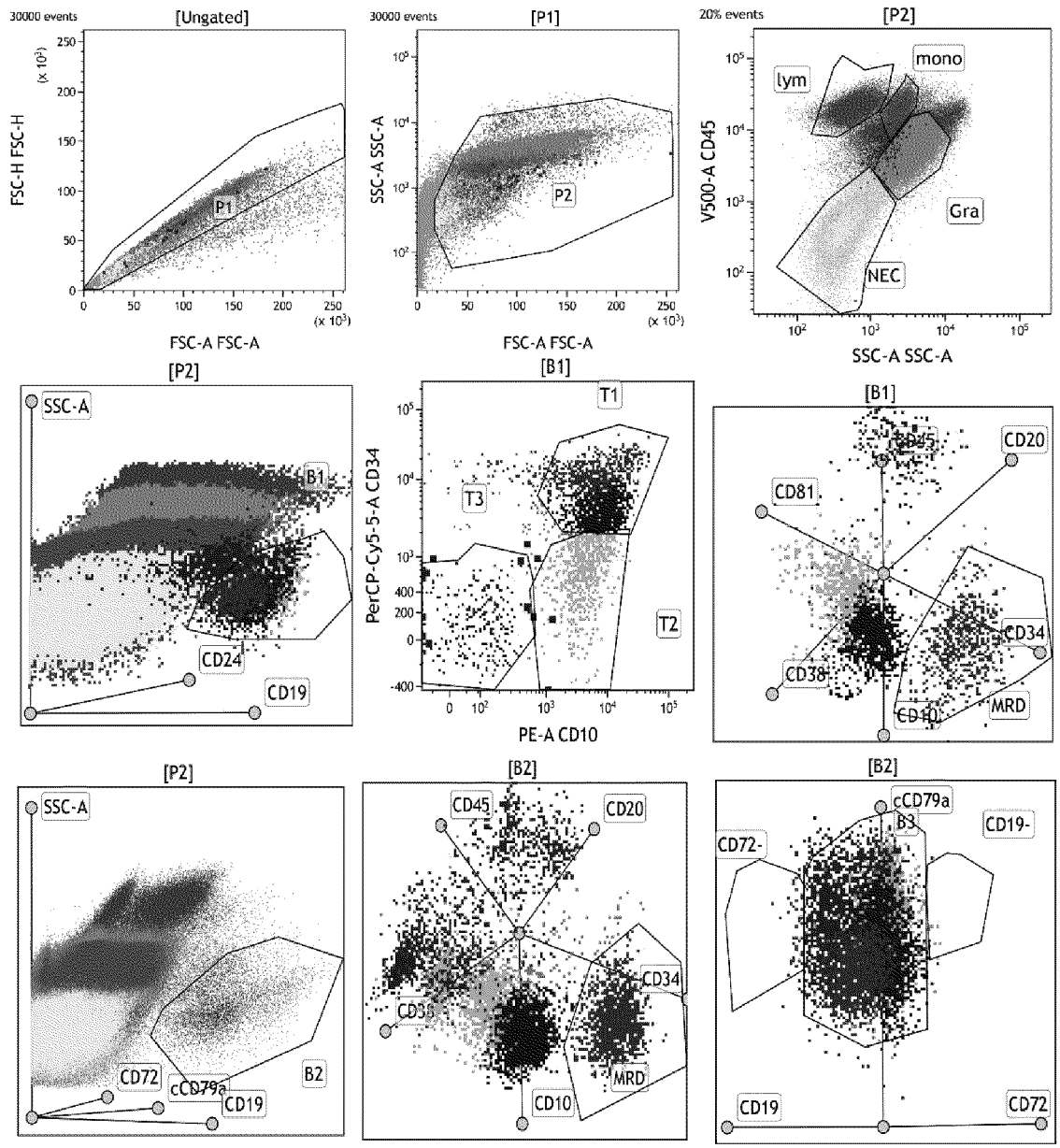

Specifically, FIG. 4 shows the multi-parameter multi-dimensional analysis in both tubes A and B with the same bone marrow sample of the B-ALL patient with MRD positive after CD19 CAR-T therapy as shown in FIGS. 3A to 3D. A single cell gate P1 and a live cell gate P2 gate were routinely set, and then a three-parameter three-dimensional radar plot was set by CD19, CD24 and SSC to achieve the B1 cell gate within the gate P2. Within the B1 cell gate, CD38/CD10/CD34/CD20/CD45/CD81 six-parameter six-dimensional radar plot was used for observation; different from the maturing process of normal B cells, a malignant tumor cell population appeared in the lower right region. For Tube B, a single cell gate P1 and a live cell gate P2 gate were orderly set, and a four-parameter four-dimensional radar plot by CD19, CD72, cCD79a, and SSC to achieve the B2 cell gate within the gate P2. Within the B2 cell gate, a five-parameter five-dimensional radar plot of CD38/CD10/CD34/CD20/CD45 was used for observation; different from the development process of normal B cells, a malignant tumor cell population appeared in a lower right region. Within the gate B2, a three-parameter three-dimensional radar plot was set using CD19, CD72, and cCD79a to detect CD19neg or CD72neg cell populations. It was seen that CD72neg were normal plasma cells and CD19neg had a small subset of malignant primitive cells.

Clinical validation was done by using the method of this example. At Hebei Yanda Lu Daopei Hospital, CAR-T clinical trials started from 2015, and nearly 1300 refractory/relapsed B-ALL cases were treated by CD19-CAR-T until August 2021, with a clinical remission rate of 91.3%. However, the current CD19neg or partially CD19neg relapse rate after CAR-T, especially CD19-CAR-T therapy, is as high as 13%-68%, as reported in the literature (60% overall according to the statistics from Hebei Yanda Lu Daopei Hospital). Although CD19 was used in combination with CD22-CAR-T in some cases, both clinical and cooperative CAR-T companies were trying to find more targets. In addition, in view of MRD detection, despite of the excellent efficacy of the cCD79a gating approach, it was found during the promotion and development thereof that the workload of manual analysis done thus far was tremendous and there was an urgent need for an efficient analysis method by applying artificially intelligence, at least with a certain prototype, that requires a multi-parameter combinational solution with high sensitivity. With the MRD detection using the method of the present invention, 200 patients were tested, with MRD testing more than 350 bone marrow samples so far, and morphological, genetic and clinical manifestation methods were used for simultaneous validation, showing a sensitivity of the method of the present invention for MRD detection of $10^{-4}$ as well as a coverage and specificity close to 100%. The false-positive rate was 0.6% and the false-negative rate was 0.3%. In addition, the multi-dimensional analysis method of the present invention is simple and easily operated, which can increase the analysis efficiency by 30%-40%. Particularly, the present invention provides a marker CD72 which is comparable to CD19 both in terms of setting B cell gate for flow cytometry MRD detection and as a promising CAR-T target, with a sensitivity (97.73%), specificity (89.73%, i.e. CD72 expression rate in T-ALL and AML, MM tumors that do not normally express CD72), and expression intensity no less than that of CD19, which may be used as post-targeted therapy gating marker and also as a promising target highly effective for further targeted therapy in CD19neg or partially CD19neg relapsed cases. Moreover, in normal samples, the CD72 marker is only expressed on B cells, but not on plasma cells, which has better specificity than CD19, and the residual plasma cells may provide security to the humoral immune system of the body, from which a smaller side effect than CD19 may be expected.

Table 2 shows the expression rate of CD72 in 193 post-targeted therapy samples collected and tested by the inventors in the present application from October 2020 to August 2021 at Hebei Yanda Lu Daopei Hospital. After extensive research and repeated testing and analysis of multiple samples, CD72, a marker with sensitivity, specificity, and expression intensity no less than CD19, was found to be both a good B cell gating marker after post-targeted therapy and a promising breakthrough target for malignancies, especially B-cell tumors, in addition to CD19.

TABLE 2

Expression rate of CD72 in samples after targeted therapy in 193 patients at Yanda Lu Daopei Hospital, Hebei

| Diagnosis | CD72-positive ratio (number of cases/total number of cases) | CD72 positivity rate (%) |
|---|---|---|
| B-ALL | 129/132 | 97.73% |
| B-NHL | 32/32 | 100% |
| burkitt | 3/3 | |
| CLL | 5/5 | |
| DLBCL | 8/8 | |
| FL | 2/2 | |
| HCL | 1/1 | |
| LPL | 1/1 | |
| MCL | 4/4 | |
| MZL | 7/7 | |
| SLL | 1/1 | |
| T-ALL | 1/7 | 14.29% |
| MPAL | 2/5 | 40% |
| AML | 14/129 | 10.85% |
| MM | 0/10 | 0 |

Remarks: B-ALL: B-cell acute lymphoblastic leukemia;
B-NHL: B-cell non-Hodgkin's lymphoma (B-lineage mature lymphocytic neoplasm);
burkitt: Burkitt's lymphoma;
CLL: chronic lymphocytic leukemia;
DLBCL: diffuse large B-cell lymphoma;
FL: follicular lymphoma;
HCL: hairy cell leukemia;
LPL: lymphoplasmacytic lymphoma.
MCL: mantle cell lymphoma;
MZL: marginal zone lymphoma;
SLL: small cell lymphoma.
T-ALL: T-cell acute lymphoblastic leukemia;
MPAL: mixed phenotypeacute leukemia;
AML: acute myeloid leukemia;
MM: multiple myeloma.

It can be seen that the positive rate of CD72 in B-cell acute lymphoblastic leukemia (B-ALL) was 97.73%, and CD72 had higher specificity than CD19 and was not expressed on both normal and malignant plasma cells. CD72 expression rates in other diseases were 100% for B-lineage mature lymphocytic neoplasms (including Burkitt's lymphoma (burkitt), chronic lymphocytic leukemia (CLL), diffuse large B-cell lymphoma (DLBCL), follicular lymphoma (FL), hairy cell leukemia (HCL), lymphoplasmacytic lymphoma (LPL), mantle cell lymphoma (MCL), marginal zone lymphoma (MZL), and small cell lymphoma (SLL)), 14.29% for T-cell acute lymphoblastic leukemia (T-ALL), 40% for mixed phenotype acute leukemia (MPAL, but 100% on malignant cells involved B immunephenotype), and 10.85% for acute myeloid leukemia (AML). Therefore, CD72 can be used as a therapeutic target alone or in combination with other markers such as CD19 and/or CD22 and BAFFR for the treatment of CD72-positive B-cell acute lymphoblastic leukemia, B-lineage mature lymphocytic tumors, T-cell acute lymphoblastic leukemia, mixed phenotype acute leukemia, acute myeloid leukemia, and other malignancies expressing CD72. For specific applications, CD72 immunotherapy can be used as an alternative for CD19 immunetherapy in the B-ALL and B-cell lymphomas cases where CD19 is weakly expressed or lost after CD19-CAR-T or a targeted therapy, or in combination with CD19-CAR-T or other therapies.

In the study of the present invention, it was found that 10.85% of AML and 40% of MPAL (but 100% on malignant cells involved B immunephenotype) express CD72, and these patients could quite possibly be put into remission with CD72-CAR-T at a time when no effective target has been found for AML, especially for MPAL with a high degree of malignancy. More importantly, CAR-T therapy and targeted drug therapy for B-ALL currently achieve over 90% remission rates, but has much poorer efficacy for B-cell lymphoma. In the study of the present invention, CD72 was found to have 100% coverage in various common B-cell lymphomas (B-NHL), higher than 98% for CD19, and had higher intensity of expression than that of CD19, especially in follicular lymphoma, a lymphoma with typically CD19dim. In addition, CD72 is expressed only on B cells, but not on plasma cells and a small number of normal mature B cells, so it could be reasonably expected, in terms of specificity, that it would have fewer side effects after CD72-CAR-T therapy than those of CD19-CAR-T. In case of relatively high CD19-CAR-T relapse rates, CD72-CAR-T will likely become an effective treatment for B-cell lymphoma, either used alone or in combination with other therapies.

What is claimed is:

1. A reagent combination for detecting B-cell tumor after targeted therapy by flow cytometry, comprising a first group of antibodies, a second group of antibodies, and a third group of antibodies, wherein each antibody is a fluorescently-labeled monoclonal antibody; wherein:
    the first group of antibodies consists of: an anti-CD38 antibody labeled with FITC, an anti-CD10 antibody labeled with PE, an anti-CD34 antibody labeled with PerCP-Cy5.5, an anti-CD19 antibody labeled with PE-Cy7, an anti-CD24 antibody labeled with APC, an anti-CD20 antibody labeled with APC-Cy7, an anti-CD81 antibody labeled with BV421, and an anti-CD45 antibody labeled with V500; the first group of antibodies being contained in a first container;
    the second group of antibodies consists of: an anti-CD38 antibody labeled with FITC, an anti-CD10 antibody labeled with PE, an anti-CD34 antibody labeled with PerCP-Cy5.5, an anti-CD19 antibody labeled with PE-Cy7, an anti-CD20 antibody labeled with APC-Cy7, an anti-CD72 antibody labeled with BV421, and an anti-CD45 antibody labeled with V500; the second group of antibodies being contained in a second container;
    the third group of antibodies consists of: an anti-cytoplasmic CD79a antibody labeled with APC; the third group of antibodies being contained accommodated in a third container;
    wherein the B-cell tumor is B-cell acute lymphoblastic leukemia or B-cell non-Hodgkin's lymphoma.

2. The reagent combination according to claim 1, wherein:
    the first group of antibodies is a mixture of the anti-CD38 antibody, anti-CD10 antibody, anti-CD34 antibody, anti-CD19 antibody, anti-CD24 antibody, anti-CD20 antibody, anti-CD81 antibody, and anti-CD45 antibody mixed in a volume ratio of 5:5:5:3:2:3:3:3, respectively; and
    the second group of antibodies is a mixture of the anti-CD38 antibody, anti-CD10 antibody, anti-CD34 antibody, anti-CD19 antibody, anti-CD20 antibody, anti-CD72 antibody, and anti-CD45 antibody mixed in a volume ratio of 5:5:5:3:3:3:3, respectively.

3. A kit for flow cytometric detection of B-cell tumor after targeted therapy, comprising the reagent combination of claim 1 and instructions for use in a two-tube parallel protocol, wherein the second group of antibodies and the third group of antibodies are used in the same sample tube, wherein the B-cell tumor is B-cell acute lymphoblastic leukemia or B-cell non-Hodgkin's lymphoma.

4. The kit according to claim 3, wherein:
    the first group of antibodies is a mixture of the anti-CD38 antibody, anti-CD10 antibody, anti-CD34 antibody, anti-CD19 antibody, anti-CD24 antibody, anti-CD20 antibody, anti-CD81 antibody, and anti-CD45 antibody mixed in a volume ratio of 5:5:5:3:2:3:3:3 respectively; and
    the second group of antibodies is a mixture of the anti-CD38 antibody, anti-CD10 antibody, anti-CD34 antibody, anti-CD19 antibody, anti-CD20 antibody, anti-CD72 antibody, and anti-CD45 antibody mixed in a volume ratio of 5:5:5:3:3:3:3, respectively.

5. The reagent combination according to claim 1, wherein the B-cell tumor is a B-cell non-Hodgkin's lymphoma selected from Burkitt's lymphoma, chronic lymphocytic leukemia, diffuse large B-cell lymphoma, follicular lymphoma, hairy cell leukemia, lymphoplasmacytic lymphoma, mantle cell lymphoma, marginal zone lymphoma, and small cell lymphoma.

6. The kit according to claim 3, wherein the B-cell tumor is a B-cell non-Hodgkin's lymphoma selected from Burkitt's lymphoma, chronic lymphocytic leukemia, diffuse large B-cell lymphoma, follicular lymphoma, hairy cell leukemia, lymphoplasmacytic lymphoma, mantle cell lymphoma, marginal zone lymphoma, and small cell lymphoma.

* * * * *